United States Patent [19]
Elkhoury

[11] Patent Number: 5,919,473
[45] Date of Patent: Jul. 6, 1999

[54] METHODS AND DEVICES FOR DELIVERING OPIOID ANALGESICS TO WOUNDS VIA A SUBDERMAL IMPLANT

[76] Inventor: George F. Elkhoury, 1561 Ramillo Ave., Long Beach, Calif. 90815

[21] Appl. No.: 08/854,323

[22] Filed: May 12, 1997

[51] Int. Cl.⁶ .................................................. A61F 13/00
[52] U.S. Cl. ..................... 424/422; 424/423; 424/426; 424/443; 424/444; 606/228; 606/229; 606/230
[58] Field of Search .................................... 424/443, 444, 424/422, 423, 426; 606/228, 229, 230

[56] References Cited

U.S. PATENT DOCUMENTS

| | | | |
|---|---|---|---|
| 3,275,510 | 9/1966 | Magid et al. | 514/282 |
| 3,728,839 | 4/1973 | Glick | 53/425 |
| 3,849,185 | 11/1974 | Shepherd et al. | 427/2.31 |
| 3,991,766 | 11/1976 | Schmitt et al. | 606/230 |
| 4,024,871 | 5/1977 | Stephenson | 606/231 |
| 4,175,326 | 11/1979 | Goodson | 52/274 |
| 4,373,217 | 2/1983 | Draenert | 623/16 |
| 4,416,886 | 11/1983 | Bernstein | 514/282 |
| 4,450,150 | 5/1984 | Sidman | 424/424 |
| 4,464,378 | 8/1984 | Hussain | 514/282 |
| 4,493,848 | 1/1985 | Lehann et al. | 514/267 |
| 4,582,052 | 4/1986 | Dunn et al. | 128/839 |
| 4,626,539 | 12/1986 | Aungst et al. | 514/282 |
| 4,708,870 | 11/1987 | Pardini | 424/405 |
| 4,764,377 | 8/1988 | Goodson | 424/435 |
| 4,806,341 | 2/1989 | Chien | 424/448 |
| 4,871,750 | 10/1989 | Roberts | 514/328 |
| 4,897,260 | 1/1990 | Ross et al. | 424/59 |
| 5,019,096 | 5/1991 | Fox et al. | 623/1 |
| 5,069,909 | 12/1991 | Sharma | 424/449 |
| 5,149,538 | 9/1992 | Granger | 424/449 |
| 5,226,912 | 7/1993 | Kaplan et al. | 606/224 |
| 5,240,711 | 8/1993 | Hille | 424/448 |
| 5,282,829 | 2/1994 | Hermes | 606/219 |

(List continued on next page.)

FOREIGN PATENT DOCUMENTS 9213540  8/1992  WIPO .

OTHER PUBLICATIONS

Lesser, G. J., et al, Pain, in vitro and in vivo studies of subcutaneous hydromorphone implants designed for the treatmentof cancer pain, vol. 65, (1996), pp. 265–272.

"Intra–articular morphine for pain relief after knee arthroscopy," G.P. Joshi et al. *The Journal of Bone and Joint Surgery*, vol. 74–B, No. 5, Sep. 1992, pp. 749–751.

English Language Abstract of WO 9213540–A1, dated Feb. 6, 1991.

Back et al. "Analgesic Effect of Topical Opioids on Painful Skin Ulcers," in Journal of Pain and Symptom Management, vol. 10, No. 7, Oct. 1995.

Basbaum et al., "Opiate Analgesia,"N. Engl. J. Med., 325:1168–1169, 1991.

Dickenson, "Neurophysiology of Opioid Poorly Responsive Pain," Cancer Surveys vol. 21: Palliative Medicine: Problem Areas in Pain and Symptom Management, 1994, pp. 5–16.

Gates and Holloway, "A Comparison of Wound Environments,"Ostomy/Wound Management, Oct. 1992, vol. 38 No. 8.

Giardina et al., "Central and Peripheral Analgesic Agents: Chemical Strategies for Limited Brain Penetration in Kappa–Opioid Agonists Belonging to Different Chemical Classes," Il Farmaco, 50(6),405–418 (1995), pp. 405–418.

Herz, "Role of Immune Processes in Peripheral Opioid Analgesia," in The Brain Immune Axis and Substance Abuse, Plenum Press, New York, 1995, pp. 193–199.

(List continued on next page.)

*Primary Examiner*—D. Gabrielle Brouillette
*Attorney, Agent, or Firm*—Greenblum & Bernstein P.L.C.

[57] ABSTRACT

An analgesic agent delivery system and method of treating postoperative pain comprising an analgesic agent such as morphine and an extended-release drug delivery device. The device may be placed in the vicinity of a wound and then provide an extended-release of the analgesic agent over a period of time, thereby controlling the pain emanating from the wound.

30 Claims, 6 Drawing Sheets

U.S. PATENT DOCUMENTS

| | | | |
|---|---|---|---|
| 5,366,081 | 11/1994 | Kaplan et al. | 206/339 |
| 5,458,582 | 10/1995 | Nakao | 604/264 |
| 5,589,480 | 12/1996 | Elkhoury et al. | 514/282 |
| 5,660,854 | 8/1997 | Hayes | 424/450 |

OTHER PUBLICATIONS

Joris et al., "Opioid Analgesia at Peripheral Sites" Anesth, Analg. 66:1277–81, International Anesthesia Research Soc., 1987.

Jaffe and Martin, "Opioid Analgesics and Antagonists" in Goodman and Gilman's The Pharmacological Basis of Therapeutics, 8th Edition (1990).

Khoury et al., "Intraarticular Morphine, Bupivacaine, and Morphine/Bupivacaine for Pain Control After Knee Videoarthroscopy," Anesthes. 77:263–266 (1992).

Kinnman et al., "Peripherally Administrated Morphine Attenuates Capsaicin–Induced Mechanical Hypersensitivity in Humans," Anesth Analg, 1997, 84:595–599.

Makman, "Morphine receptors in immunocytes andneurons," Advances in Neuroimmunology, vol. 4, pp. 69–82, 1994.

Mather, "Opioids: A Pharmacologist's Delight!" Australasian Society of Clincal and Experimental Pharmacologists and Toxicologists Symposium, 1994, Clinical and Experimental Pharmacology and Physiology (1995) 22, 833–836.

Needham, "Painless Lumbar Surgery: Morphine Nerve Paste," Connecticut Medicine, vol. 60, No. 3, Mar. 1996, pp. 141–143.

Peyman et al., "Effects of morphine on corneal sensitivity and epithelial wound healing: implications for topical ophthalmic analgesia,"LSU Eye Center, Louisiana State University Medical Center School of Medicine, Accepted for publication Aug. 26, 1993.

Regan, "The Use of Intrasite Gel in Healing Open Sternal Wounds,": Ostomy/Wound Management, Apr. 1992, vol. 38 No. 3, pp. 15–21.

Reisine and Pasternak, "Opioid Analgesics and Antagonists," in Goodman and Gilman's The Pharmacological Basis of Therapeutics, Ninth Edition, Chapter 23, pp. 521–544, 1996.

Schwartz and Wiseman, "Surgical Supplies," Chapter 108, pp. 1873–1882, 1990.

Siddall et al., "Pain Mechanisms and Management: An Update," Clinical Experimental Pharmacology and Physiology (1995) 22, 679–688.

Stein et al., "Antinociceptive effects of mu–and kappa–agonists in inflammation are enhanced by a peripheral opioid receptor–specific mechanism of action," Eur. J. Pharmacol. 155:255–264 (1988).

Stein, "The Control of Pain in Peripheral Tissue by Opioids," Mechanisms of Disease, Jun. 22, 1995, vol. 332, No. 25, pp. 1685–1690.

Stein et al., "No Tolerance to Peripheral Morphine Analgesia in Presence of Opioid Expression in Inflamed Synovia," J. Clin. Invest., vol. 98, No. 3 Aug. 1996, 793–799.

Stein et al., "Opioids as novel intro–articular agents in arthritis," in Progress in Pain Research and Management, Fields, H.L., and Liebeskind, J.C., eds., 1:289–296, IASP Press, Seattle (1994).

Stein et al., "Peripheral and non–neuronal opioid gffects," Curr. Opin. Anasth. 7:347–351 (1994).

Stein et al., "Peripheral effect of fentanyl upon noiception in inflamed tissue of the rat," Neurosci. Lett. 84:225–228 (1988).

Stein, "Peripheral Mechanisms of Opioids Analgesia" Anesth. Analg. (1993), pp. 182–191.

Stein et al., "Peripheral Opioid Receptors," Annals of Medicine 27:219–221, 1995.

Stein et al., "Analgsic Effect of Intracellular Morphine After Arthroscopic Knee Surgery," N. Engl. J. Med., 325:1123–1126 (1991).

Tennant et al., "Topical Morphine for Peripheral Pain" in the Letters to the Editor in The Lancet vol. 342 (1993) pp. 1047–1048.

Thomas, "In Vitro Investigations of a New Hydrogel Dressing," Journal of Wound Care, Mar. 1996, vol. 5 No. 3, pp. 130–131.

Thompson and Pierce, "Local Analgesia with Opioid Drugs," The Annals of Pharmacotherapy, Feb. 1995, vol. 29, pp. 189–190.

Traynor, "Opioid Receptors and Their Subtypes: Focus on Peripheral Isolated Tissue Preparations,"Neurochem, Int., vol. 24, No. 5, pp. 427–432, 1994.

Williams, "Intrasite Gel: a hydrogel dressing, 1994".

"DepoMorphine Investigational New Drug Application Filed," Press Release from DepoTech Corp., Dec. 9, 1996, http://www.pslgroup.com/dg/eafa.htm.

"Under Skin Pain Implant Developed," Press Release from Johns Hopkins Medical Institutions, Jul. 25, 1996, http://www.ari.net/newswise/articles/PAINPOL.JHM.html.

METHODS AND DEVICES FOR DELIVERING OPIOID ANALGESICS TO WOUNDS VIA A SUBDERMAL IMPLANT

BACKGROUND OF THE INVENTION

1. Field of the Invention

This invention relates to a method, composition, and apparatus for relief of pain. More specifically, this invention relates to a method, composition, and apparatus for treating pain associated with wounds (surgical or nonsurgical) or inflamed/painful areas (e.g., cancer), as well as delivery systems and methods for delivering opioid analgesics directly to wounds (surgical or nonsurgical) or inflamed/painful areas (e.g., cancer). Delivery systems of some embodiments of the present invention preferably comprise those which can be intimately associated with a wound, including but not limited to, sutures, surgical staples, trocars, and implants, such as rods or pellets. Delivery systems of other embodiments of the present invention also may preferably comprise external wound dressings and wound closures including but not limited to, bandages, surgical dressings, gauzes, and sterile adhesive strips. The delivery systems allow for the delivery of opioids and/or other narcotic analgesics to the site of the wound over an extended period of time.

2. Background of the Invention and Related Art

Morphine is the prototype of the class of opioid analgesics which can exert a centrally-mediated analgesic effect by activating opioid receptors within the brain. Morphine has been used for centuries and is unsurpassed as an analgesic for severe pain. However, morphine has a number of serious side effects which hamper its widespread use and acceptance by physicians and patients. Morphine's side effects (and/or side effects of other opioid analgesic agents) include addiction, nausea, respiratory depression, somnolence, and dysphoria, all of which are mediated by morphine's action within the central nervous system. In addition, the development of tolerance and physical dependence with repeated use is a characteristic side effect of all opioid drugs. Major research efforts have been directed toward development of morphine-like drugs that act within the brain and are devoid of the undesirable side effects but that retain the desirable potent analgesic effects. However, these efforts have been relatively unsuccessful and there has been continuing need for improvement.

Conventional therapy for pain (surgical and nonsurgical) includes the use of oral, intramuscular, intravenous, epidural, and intrathecal morphine which travels through the bloodstream to reach opioid receptors in the brain, or interacts with opioid receptors directly in the central nervous system. The side effects described in the literature (including death) are almost completely attributable to these drugs' actions in the central nervous system.

Due to severe postoperative pain, many patients will have an extended stay in the hospital solely for control of the severe pain. Consequently, patients often receive significant amounts of opioids intravenously or intramuscularly, which can often result in side effects which include respiratory depression, nausea, vomiting, dysphoria, and a significant decrease in blood pressure. The side effects often necessitate the concomitant use of other medications just to control them. Furthermore, a prolonged stay in the hospital can increase the infection rate due to a high incidence of resistant pathogens in the hospital.

In contrast, patients who have adequate pain control without side effects can leave the hospital sooner and recover at home. The economic implications for the health care system are a decreased incidence of nosocomial infections as well as side effects and consequently a significant reduction in the cost of surgery.

Because of their potent centrally-mediated (brain and spinal cord) analgesic effects, intravenous administration of opioids has remained the route of choice. However, none of the conventional routes of administration has provided an acceptable system for delivering optimally effective levels of an analgesic substance without the detrimental side effects. In addition, it appears that optimal release of those medications has also not been established. It would, therefore, be desirable to derive the analgesic benefits of this class of opioids without the detrimental side effects that are primarily attributable to its actions within the brain.

In addition to their presence in the brain, opioid receptors have been found on sensory nerves in inflamed subcutaneous tissue. This finding was reported in Stein et al., "Peripheral effect of fentanyl upon nociception in inflamed tissue of the rat," *Neurosci. Lett.* 84:225–228 (1988), and in Stein et al., "Antinociceptive effects of mu- and kappa-agonists in inflammation are enhanced by a peripheral opioid receptor-specific mechanism of action," *Eur. J. Pharmacol.* 155:255–264 (1988). Small doses of opioids, when applied locally or topically in inflamed areas outside the central nervous system, can produce local analgesic effects by interacting with the opioid receptors on peripheral sensory nerves and producing local analgesia. This finding was discussed in Stein et al., "Opioids as novel intra-articular agents in arthritis," In: *Progress in Pain Research and Management*, Fields, H. L., and Liebeskind, J. C., eds., 1:289–296, IASP Press, Seattle, (1994).

Peripheral opioid effects are not initially apparent in normal tissue, but do become apparent within minutes to hours at the site of inflammation. It is believed that the reason for the pain relief is that opioids can gain easier access to neuronal opioid receptors during inflammation as a result of the disruption of the perineurium (which is normally an impermeable sheath encasing the peripheral nerve fiber). Further, the number of peripheral sensory nerve terminals is increased in inflamed tissue and a phenomenon known as sprouting occurs in which the number of fibers increases significantly within inflamed tissue. The sprouting results in a subsequent increase in the number of morphine receptors that are peripherally accessible to locally-applied opioids.

The peripheral opioid effects are observed to be much more pronounced in inflamed than non-inflamed tissue, and this constitutes an advantage according to the present invention since inflammation is associated with surgery. In addition, it has been determined that small doses of conventional opioid drugs such as morphine, or other opioids, can produce potent analgesic effects after local application to inflamed tissues.

In accordance with the present invention, it has been determined that opioid receptors can be directly targeted in peripheral tissue (local analgesia) rather than dosing to affect opioid receptors in the brain. Importantly, the doses of an opioid analgesic required to produce analgesia in the periphery (local analgesia) are extremely small and, therefore, are substantially devoid of the above-mentioned, centrally-mediated side effects.

The topical application of opioids for the treatment of pain is disclosed in U.S. Pat. No. 5,589,480, to ELKHOURY et al., the entire contents of which are hereby incorporated by reference as though set forth in full herein. ELKHOURY et al. discloses the topical application of opioids in vehicles which do not promote the transdermal migration of the drug. ELKHOURY et al. discloses the treatment of external skin lesions and burns by such treatment. ELKHOURY et al. also discloses the use of such a formulation on mucosal membranes, including those of the mouth and throat. A clinical demonstration of such application is presented in "Analgesic Effect of Topical Opioids on Painful Skin Ulcers," by Back et al., in *Letters to the Editor, Journal of Pain and Symptom Management*, Vol. 10, No. 7, October 1995, wherein it was shown that diamorphine applied in an occlusive wound dressing could relieve the pain associated with decubitus ulcers and malignant skin ulcerations.

Although the topical application of opioids, as described in ELKHOURY et al., is appropriate for the aforementioned ailments, such as skin lesions and burns, topical application would likely be ineffective for surgical and other wounds. Wounds, by their nature, are in intimate contact with the blood stream and blood supply. Plasma and blood fluids are critical to the wound healing process as they supply the necessary materials, including blood cells as well as different factors involved in the complex reparative mechanism. Blood brings oxygen and growth factors and removes anoxic and damaged materials. In addition, it would likely absorb any locally applied opioid after only a short period of time, thereby rendering it ineffective.

A surgical incision comprises several layers: skin, fat, fascia, muscle, connective tissue, etc. Often, each layer requires suturing for wound closure. The pain associated with surgical wounds often emanates not only from the surface skin incision, but from a deeper layer (muscle and connective tissue). These deep layers result in significant post-surgical pain. In fact, surgical trauma to muscle and fascia is the primary source of post-surgical pain. An opioid analgesic preparation, in accordance with ELKHOURY et al., applied to deep layers prior to wound closure would be expected to be rapidly cleared from the area, providing only short-term pain relief, if any.

The present invention addresses the problems posed in the aforementioned case by providing a device and/or method whereby an analgesic may be delivered to the origin of pain over an extended period of time. The present invention, in the form of surgical sutures, pellets, staples, etc., can be placed even at the deepest of incisions or even at the skin, providing excellent relief of pain resulting from skin or deep wounds (surgical or nonsurgical). The present invention, in the embodiment of a suture or staple with an opioid analgesic incorporated or impregnated therein, could be used to close surgical wounds. The analgesic agent may be incorporated into a polymeric material, of which the suture, pellet, or staple is made. Alternatively, the opioid analgesic agent may be incorporated into a suture material which is not absorbable, such as nylon. In either embodiment, the opioid analgesic agent is released from the suture in minimal amounts and over an extended period of time, providing relief of pain. Similarly, pellets of an absorbable material, with an opioid analgesic incorporated therein, could be sprinkled into a wound at different layers prior to closure. The present invention provides an apparatus and method whereby an analgesic may be delivered to a local area, without significant systemic absorption, and thereby providing local analgesia.

The medical field contains examples of devices which deliver medicaments to a body. Examples include drug-containing sutures, staples, pellets, and the like. U.S. Pat. No. 3,991,766, to SCHMITT et al., discloses the use of a polyglycolic acid polymer in surgical sutures, clips, and storage pellets, which can be used alone or with a medicament contained within. Acceptable medicament classes listed by SCHMITT include antibiotics, antiseptics, anesthetics, antioxidants, as well as steroid hormones. Similarly, U.S. Pat. No. 5,019,096, to FOX et al., discloses matrix-forming polymers which contain antimicrobial agents. Fibrous articles, including threads, or intrauterine devices, which are used to deliver povidone iodine, are disclosed in U.S. Pat. No. 4,582,052, to DUNN et al. U.S. Pat. No. 4,024,871, to STEPHENSON, discloses sutures which are impregnated with an antibiotic. U.S. Pat. No. 4,764,377, to GOODSON, discloses implants impregnated with antibiotics, and which are to be used in periodontal disease. Other implants which can be used to deliver drugs subdermally are disclosed in U.S. Pat. No. 5,366,081, to KAPLAN et al., and in U.S. Pat. No. 5,282,829, to HERMES. For their disclosure of the manner and process for making surgical devices, including sutures and implants, the contents of SCHMITT (U.S. Pat. No. 3,991,766), FOX (U.S. Pat. No. 5,019,096), DUNN (U.S. Pat. No. 4,582,052), STEPHENSON (U.S. Pat. No. 4,024,871), GOODSON (U.S. Pat. No. 4,764,377), KAPLAN (U.S. Pat. No. 5,366,081), and HERMES (U.S. Pat. No. 5,282,829) are hereby incorporated by reference as though set forth in full herein.

Opioid drugs are characterized not only by their analgesic properties, but also by their ability to cause physical dependence and tolerance through a centrally-mediated mechanism. Tolerance results in a need to increase the dose necessary to produce centrally-mediated analgesia. Because of the need to increase the dose, an implantable drug depot device delivering an opioid in a centrally-effective dose would quickly become ineffective in its ability to produce analgesia. For this reason, implantable extended-release opioid delivery devices, while available, are not very useful.

Based on several published studies, strong evidence now exists demonstrating that opioid receptors are present in areas of inflamed tissue. Analgesia has been reported with morphine injections into a closed space, such as in the knee of arthritic patients. See, as examples of such studies, Khoury et al., *Anesthes.* 77: 263–266 (1992); Stein et al., *N. Engl. J. Med.*, 325:1123–1126 (1991); and Basbaum, et al., *N. Engl. J. Med.*, 325: 1168–1169 (1991). However, such practice is relatively restricted by the fact that the treatment generally requires administration by a qualified physician. In addition, for continued relief, repeated injections are necessary.

Like the pain emanating from an afflicted joint in arthritis, the pain associated with a wound is significant and debilitating. Frequently, hospital stays following surgery are extended because the surgical patient continues to require the administration of significant amounts of an opioid analgesic agent for relief of the severe pain. Extended stays, in turn, result in greatly increased medical bills.

A feature unique to the treatment of localized pain is the minimal amount of opioid analgesic agent required to bring about local analgesia. Apparently, the inflamed area in the locality of the pain exhibits an increased sensitivity to the antinociceptive effects of opioid analgesic agents, possibly because of activation of peripheral opioid receptors located on primary afferent neurons. The activation may occur via several means: de novo synthesis of opioid receptors, resulting in an increase in the total number of opioid receptors in the area; axonal transport of pre-existing opioid receptors to the nerve terminal, similarly increasing the total number of opioid receptors in the area; some other process of activating pre-existing opioid receptors by the inflammatory process. A discussion of such mechanisms is presented in Stein, "Peripheral and non-neuronal opioid effects," *Curr. Opin. Anaesth.* 7:347–351 (1994).

Regardless of the mechanism by which opioid sensitivity is increased, methods are known by which pain can be modulated at peripheral sites. However, such existing treatments, including intra-articular administration of opioid analgesic agents, are limited by the fact that treatments must be applied frequently, because the opioid analgesic effect commonly has a duration of only 8 hours after injection. Even a long-lasting opioid, such as methadone, is usually only effective for less than 24 hours. Prolonged pain relief following surgery has been demonstrated, but such relief is often provided by routes of administration including targeting central nervous system receptors. Specifically, an article published in *Connecticut Medicine*, (Vol. 60, No. 3, March, 1996), and authored by Charles Needham, shows prolonged relief of pain following lumbar surgery. The Needham article discloses the use of a morphine nerve paste applied to the dura in the epidural space (central nervous system) and nerve roots to relieve post-surgical pain. Pain relief from the morphine applied in the epidural space (centrally-mediated) is very likely an important component of the analgesic effect demonstrated by Needham. However, the author indicates that peripheral opioid receptors could also be involved in the resulting postoperative pain relief.

The present invention addresses the foregoing problem, that is, the present invention provides a method whereby peripheral opioid receptors may be targeted, and whereby repeated administration is not necessary. The present invention provides a level of relief of the deep pain associated with trauma, as well as other conditions (e.g., cancer) that is quite unexpected. Because of the ability of the present invention to deliver the analgesic directly to the pain receptors at the site of the wound, a lower than normal dose of analgesic is needed. In fact, the present invention delivers doses that are too low to produce analgesia in a centrally-mediated manner. The use of a lower dose avoids all of the detrimental centrally-mediated side effects associated with systemic administration of the analgesic. Consequently, the present invention is a breakthrough in the field of relief of surgical pain and other pains.

SUMMARY OF THE INVENTION

In view of the foregoing, it is an object of the present invention to provide a method of relieving pain mediated by pain receptors located beneath the skin, which relief is maintained for an extended period of time.

It is another object of the invention to provide a method of delivery of analgesics to a local area which method comprises placing a delivery device containing the opioid analgesic under the skin.

It is another object of the invention to provide an apparatus or device which may be used to deliver analgesics locally to an area under the skin.

It is another object of the invention to provide an apparatus or device which may be used to deliver analgesics locally to an area under the skin for an extended period of time.

It is another object of the present invention to provide a method of relieving the pain of surgical wounds, preferably deep surgical wounds, which method comprises placing an analgesic delivery device in the locality of the wound and delivering the analgesic directly to peripheral opioid receptors.

According to an aspect of the present invention, an opioid analgesic delivery device is placed within the wound in such a manner that the tissues in the site of surgery will come in intimate contact with the analgesic. The active agent is released freely at the site of inflammation eliminating the variability inherent in long diffusional pathways associated with intravenous or intramuscular treatment. By controlling release characteristics of the drug delivery system, with duration of contact and drug concentration, the invention provides sustained delivery over a period of time which will result in complete local analgesia within the site of surgery. The method and apparatus of the present invention employ this principal to treat postoperative surgical pain with the advantage of long-lasting effectiveness and superior postoperative pain relief compared to conventional methods.

In one preferred embodiment, an analgesic agent delivery and maintenance system (also referred to herein as a delivery device or apparatus) suitable for continuously delivering a pharmacologically-effective level of analgesic to the site of an incision includes an opioid analgesic agent and a biocompatible polymeric material. The polymeric material contains the analgesic drug or agent that, in one preferred embodiment, is impregnated in the polymeric matrix. Preferably, the polymeric material is permeable to the analgesic drug or agent so that the drug or agent can diffuse out of the matrix continuously over an extended period of time. The polymeric matrix containing the analgesic drug or agent in accordance with one preferred embodiment of the invention is a fiber having a diameter in the range of from about 0.1 to about 1 mm, and this fiber is sufficiently flexible to conform readily to the surgical site to be treated. Preferably, such analgesic drug or agent delivery and maintenance system places the analgesic drug or agent in and around the sutures at the incision to provide a delivery and a release system that is continuously operational over five to ten days postoperatively while maintaining a significant therapeutic level of the analgesic agent at the surgical site (local analgesia).

The foregoing and other objects of the invention are achieved by the provision a method of inducing analgesia, comprising delivering via a single administration, and for a period of time which is at least about 2 days, a therapeutically-effective amount of an opioid analgesic agent to peripheral opioid receptors, which amount is ineffective for the production of centrally-mediated analgesia, and wherein the analgesia is produced in the substantial absence of delivery to centrally-located opioid receptors. In preferred embodiments, the period of time is at least about 7 days. In more preferred embodiments, the period of time is at least about 15 days. In more preferred embodiments, the period of time is at least about 30 days. In more preferred embodiments, the period of time is at least about 45 days.

The foregoing and other objects of the invention are further achieved by the provision of a method of inducing analgesia, comprising delivering, for a period of time which is at least about 1 day, via an at least partially subdermal drug delivery device, a therapeutically-effective amount of an opioid analgesic agent to peripheral opioid receptors, which amount is ineffective for the production of centrally-mediated analgesia. Preferably, the device comprises a polymeric material. In other preferred embodiments, the device comprises an absorbable material. Preferably, the absorbable material comprises a synthetic material, which is preferably selected from the group consisting of cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof. In other preferred embodiments, the absorbable material comprises a non-synthetic material, which is selected from the group consisting of catgut, cargile membrane, fascia lata, gelatin, collagen and combinations thereof. In still other preferred embodiments, the device comprises a nonabsorbable material. Preferably, the nonabsorbable material comprises a synthetic material, which is selected from the group consisting of nylons, rayons, polyesters, polyolefins, and combinations thereof. In other preferred embodiments, the nonabsorbable material comprises a non-synthetic material, which is selected from the group consisting of silk, dermal silk, cotton, linen, and combinations thereof. In preferred embodiments, the device comprises a surgical suture. In other preferred embodiments, the device comprises staples or clips. In still other preferred embodiments, the device comprises an implant, which is selected from the group consisting of pellets, pills, capsules, tablets, rods, ribbons, strips, and bars. In still other preferred embodiments, the device is selected from the group consisting of trocars, catheters, and tubes.

The foregoing and other objects of the invention are achieved by the provision of a method of inducing analgesia, comprising delivering, for a period of time which is at least about 1 day, via a surgical suture, a therapeutically-effective amount of an opioid analgesic to peripheral opioid receptors, which amount is ineffective for the production of centrally-mediated analgesia.

The foregoing and other objects of the invention are achieved by the provision of a method of inducing analgesia, comprising delivering, for a period of time which is at least about 1 day, via an implant, a therapeutically-effective amount of an opioid analgesic to peripheral opioid receptors, which amount is ineffective for the production of centrally-mediated analgesia.

The foregoing and other objects of the invention are achieved by the provision of a drug delivery device for subdermal administration comprising an opioid analgesic and a structural material, which device releases said opioid analgesic for a period of time which is at least about 1 day, and wherein a unit dosage of the device does not contain enough opioid analgesic agent to produce centrally-mediated analgesia. Preferably, the opioid analgesic comprises an opioid agonist, which is selected from the group consisting of morphine, depomorphine, heroin, hydromorphone, oxymorphone, levorphanol, methadone, meperidine, fentanyl, sufentanil, alfentanil, codeine, hydrocodone, drocode, oxycodone, and mixtures thereof. In other preferred embodiments, the opioid analgesic comprises a partial opioid agonist, which comprises ethylketocyclazocine. In other preferred embodiments, the opioid analgesic comprises a mixed opioid agonist/antagonist, which is selected from the group consisting of cyclazocine, nalbuphine, buprenorphine, meptazinol, butorphanol, pentazocine, dezocine, and mixtures thereof. In preferred embodiments, the structural material comprises an absorbable material. Preferably, the absorbable material comprises a synthetic material, which is selected from the group consisting of polyglycolic acid, copolymers of lactide and glycolide, polydioxanone, polyglactin, poliglecaprone, polyglyconate, polygluconate, and combinations thereof. In other preferred embodiments, the absorbable material comprises a non-synthetic material, which is selected from the group consisting of gelatin, collagen, and combinations thereof. In still other preferred embodiments, the structural material comprises a nonabsorbable material. Preferably, the nonabsorbable material comprises a synthetic material which is selected from the group consisting of polyesters, polyolefins, and combinations thereof. In other preferred embodiments, the nonabsorbable material comprises a non-synthetic material. In preferred embodiments, a unit dosage is from about 0.01 mg morphine/4 hr/10 cm wound to about 8 mg morphine/4 hr/10 cm wound. More preferably, a unit dosage is from about 2 mg morphine/4 hr/10 cm wound to about 6 mg morphine/4 hr/10 cm wound. Most preferably, a unit dosage is about 4 mg morphine/4 hr/10 cm wound. In preferred embodiments, the opioid analgesic agent comprises up to 90% by weight of the device. In other preferred embodiments, the opioid analgesic agent comprises up to 70% by weight of the device. In other preferred embodiments, the opioid analgesic agent comprises up to 30% by weight of the device.

The foregoing and other objects of the present invention are achieved by the provision of a method of inducing analgesia, comprising delivering for a period of time which is at least about 2 days, via an externally-applied wound dressing, a therapeutically-effective amount of an opioid analgesic, wherein delivering the opioid analgesic is ineffective for production of centrally-mediated analgesia, and wherein the analgesia is produced in the substantial absence of delivery to centrally-located opioid receptors. Preferably, the wound dressing is selected from the group consisting of surgical gauzes, dressing combines, laparotomy sponges, sanitary napkins, eye pads, gauze roller bandages, muslin bandage rolls, woven elastic bandages, crepe bandages, conforming bandages, high-bulk bandages, triangular bandages, orthopedic bandages, stockinette bandages, cast bandages, adhesive tapes, adhesive strips, and combinations thereof.

BRIEF DESCRIPTION OF THE DRAWINGS

The foregoing and other objects, features, and advantages of the invention will be apparent from the following more particular description of the preferred embodiments, as illustrated in the accompanying drawings, in which reference characters refer to the same, or like, parts throughout the various views, and wherein.

DETAILED DESCRIPTION OF PREFERRED EMBODIMENTS OF THE INVENTION

The following definitions are intended to be interpreted in an illustrative, rather than limiting sense. Therefore, they are to be interpreted inclusively, and are not to be limited to the specific definition recited.

A. Definitions

Absorbable: those materials which can be broken down or digested in animal tissues Agonist: a compound that displays an affinity for a receptor, and which enhances or stimulates the functional properties of the receptor. Examples of opioid agonists include but are not limited to, morphine, meperidine, depomorphine, methadone, etorphine, levorphanol, fentanyl, and sufentanyl.

Analgesia: relief of pain.

Analgesic: a compound that relieves pain; an opioid analgesic is an opioid that relieves pain by action on opioid receptors.

Antagonist: a compound that does not enhance or stimulate the functional properties of a receptor, yet blocks those actions by an agonist. Examples of opioid antagonists include but are not limited to naloxone and naltrexone.

Antinociceptive: see nociceptive

Bandage: a dressing used to cover an injury

Biocompatible: compatible with a living being; non-toxic.

Centrally-mediated analgesia: analgesia produced through activation of opioid receptors in the central nervous system (brain, spinal cord, epidural space, etc.).

Central opioid receptor: opioid receptor that is found in the central nervous system.

Central nervous system: the brain and spinal cord.

Wound closure: conventional materials and/or devices for closing wounds, e.g., sutures, clips, staples, etc.

Dermal: relating to the dermis.

Dermis: living part of skin.

Dressing combine: designed to provide warmth and protection and to absorb large quantities of fluid that may drain from an incision or wound; consists of a nonwoven fabric cover enclosing fiber with or without absorbent tissue.

Extended-delivery: in reference to the delivery of drugs, delivery which is extended temporally in some manner.

Inflammation: an immune system-mediated process characterized by redness, heat, swelling, and pain at the local site.

Intramuscular: within muscle; a common route of parenteral drug delivery.

Intravenous: within vein; a common route of parenteral drug delivery.

Mixed agonist-antagonist: referring to opioids, a compound which displays both agonist and antagonist activities at opioid receptors subtypes. Examples of opioids which are mixed agonist-antagonists include but are not limited to buprenorphine and butorphanol.

Nociception: the sensation of pain

Nociceptive: of, causing, or relating to pain

Opioid: those agonists and antagonists (as well as mixed agonist/antagonists and partial agonists) with morphine-like activity, as well as naturally-occurring and synthetic opioid peptides.

Opioid analgesic: opioids which produce an analgesic effect, generally through their interaction with opioid receptors; opioid analgesics may be opioid receptor agonists, opioid receptor partial agonists, or opioid receptor mixed agonist-antagonists.

Opioid receptor: a receptor at which an opioid binds. There are at least three separate subtypes of opioid receptors: mu ($\mu$), delta ($\delta$), and kappa ($\kappa$).

Partial agonist: a compound which produces some effects, but not others, at receptor subtypes which are known to be responsible for multiple effects. Ethylketocyclazocine is a partial opioid receptor agonist.

Perineurium: the sheath of dense connective tissue that envelops a bundle of nerve fibers composing a peripheral nerve.

Peripheral nervous system: cranial, spinal, and peripheral nerves which serve to provide a nervous connection between tissues and organs of the body and the brain.

Peripheral opioid receptor: opioid receptor located outside the central nervous system.

Sprouting: a phenomenon which occurs in inflammation which is characterized by an increase in the number of peripheral sensory nerve terminals as well as the number of peripheral opioid receptors.

Skin: the outer covering of an animal body; the outermost layer of skin is called the epidermis (non-living part), the layer beneath the epidermis is called the dermis (living part).

Stitch: (verb) a single complete in-and-out movement of a suture through a tissue; (noun) a single loop formed by stitching.

Subdermal: below the dermis.

Suture: (verb) the act or method of joining together edges of a wound or incision by stitching; (noun) any material, including but not limited to nylon, silk, polymer, etc., used in the act of suturing.

Therapeutically-effective amount: the amount necessary to bring about a therapeutic effect; in the case of an opioid analgesic, the amount necessary to produce analgesia.

Transdermal: passing through the dermis.

Wound: an injury to the body in which the skin or other tissue is broken, cut, pierced, torn, etc.

The use of the term "drug delivery device" herein is meant to encompass those objects which are self-supporting structures.

In addition, the phrase "at least partial subdermal administration" is meant to comprise administration in which at least some of the opioid analgesic agent is administered subdermally. Thus, this definition includes devices and configurations such as, for example, sutures, wherein a portion of the suture extends through a subdermal region and another portion of the suture extends above the dermis. Such a configuration would occur when the suture is employed as an external wound closure.

Other terms employed herein not specifically defined immediately above are well known to those of ordinary skill in the art and/or are also further defined in the specification either expressly or indirectly.

B. Preferred Embodiments

The present invention is directed to methods, devices, and compositions for delivering opioid analgesic agents to peripheral opioid receptors. Pain relief according to the present invention is preferably brought about by targeting of peripheral opioid receptors, as opposed to centrally-located opioid receptors. Preferably, embodiments of the present invention are placed in the area in and/or around the source of pain. Preferably, embodiments of the invention are placed in the area in which inflammation is already occurring, or in which inflammation is expected to occur. Alternatively, the present invention may be placed at a site of pain in which no redness or inflammation exists, yet peripheral opioid receptors are present. Such embodiments in which the invention is used in the absence of redness or inflammation are preferred as well.

In cases of cancer, it would be advantageous to place the present invention at the site of the inflamed tumor to deliver therapeutic doses of the opioid analgesic agent directly to the area. Such embodiments are also envisioned according to preferred embodiments of the present invention. The treatment of pain emanating from bone is also an additional preferred embodiment of the present invention.

Preferred embodiments of the present invention deliver the agent to the site, such that local analgesia is maintained over an extended period of time. The invention preferably delivers a small dose of the agent to the site over an extended period of time. Preferably, the invention provides relief of pain for a time significantly longer than that time of pain relief provided by a single injection of the same agent. Preferably, the pain relief is maintained for greater than one day. Maintenance of pain relief is preferably provided for between one and thirty days. Longer periods for maintenance of pain may be necessary in some situations, and such applications are also envisioned according to other preferred embodiments the present invention. Alternatively, maintenance of pain relief for periods shorter than one day may also be necessary in other situations, and such applications are also envisioned according to other preferred embodiments of the invention.

Preferred opioid analgesic agents are those which have antinociceptive effects. Preferably, the opioid analgesic agent used in accordance with the present invention comprises an opioid agonist. Opioid agonists include, but are not limited to, morphine, depomorphine, etorphine, heroin, hydromorphone, oxymorphone, levorphanol, methadone, levomethadyl, meperidine, fentanyl, sufentanil, alfentanil, codeine, hydrocodone, oxycodone, and mixtures of the foregoing. In other preferred embodiments, the opioid analgesic agent comprises a compound with mixed opioid agonist/antagonist activities, or one that exhibits only partial agonist activity. Compounds which exhibit mixed agonist/antagonist activity include, but are not limited to, buprenorphine, nalbuphine, butorphanol, pentazocine, and mixtures of such compounds. Compounds which exhibit partial agonist activity include, but are not limited to ethylketocyclazocine. Other preferred opioid analgesic agents envisioned include, but are not limited to, natural and synthetic peptides which interact with opioid receptors. The present invention is not limited to the delivery of a single opioid analgesic agent: preferred embodiments include mixtures of opioid agents which produce an analgesic effect. The present invention is also not limited to the specific drugs mentioned herein, and derivatives that are pharmaceutically-acceptable salts, prodrugs, and other derivatives are envisioned as well. It is expected that, as medical science advances, more compounds which can be classified as opioid analgesics will be discovered. Such compounds are also envisioned to be within the scope of the present invention. The present invention is not limited solely to the delivery of opioid analgesic agents: other agents may be incorporated as well, including but not limited to antibiotics and anesthetics.

It is believed that the amount of opioid analgesic agent necessary to produce an effect at the peripheral receptor is based on, or related to, the size of the area and the condition which is to be treated. For example, the amount of opioid analgesic agent needed to treat the pain in an arthritic knee is likely greater than the amount of opioid analgesic agent needed to relieve pain in a finger joint. In addition, an acute condition will need less medication for less time than a chronic condition. Other important factors include the amount of drug delivered, and the rate at which the drug is delivered. In terms of the present invention, the preferred dosage range is preferably determined by considering the amount of opioid delivered, in milligrams, the rate of delivery, in hours, and the length of the wound, in centimeters, of the wound to be treated according to the present invention. In preferred embodiments, the amount of opioid administered to the site is from about 0.01 milligrams morphine per 4 hours per 10 centimeter of wound length (0.01 mg/4 hr/10 cm wound) to about 8 mg morphine/4 hr/10 cm wound. More preferably, the dose of morphine is from about 2 mg/4 hr/10 cm wound to about 6 mg/4 hr/10 cm wound, and is most preferably 4 mg/4 hr/10 cm of wound.

The rate of delivery may be varied as well in other preferred embodiments. For example, in preferred embodiments, the invention delivers from about 4 mg morphine/1 hr/10 cm of wound to about 4 mg morphine/7 hr/10 cm wound. More preferably, the dose of morphine is from about 4 mg/3 hr/10 cm wound to about 4 mg/5 hr/10 cm wound, and is most preferably 4 mg/4 hr/10 cm of wound.

The dose may be varied by considering the length of wound as well. For example, in preferred embodiments, the invention delivers from about 4 mg morphine/4 hr/1 cm of wound to about 4 mg morphine/4 hr/20 cm wound. Preferably, the dose of morphine is from about 4 mg/4 hr/5 cm wound to about 4 mg/4 hr/15 cm wound, and is more preferably from about 4 mg/4 hr/8 cm of wound to about 4 gm/4 hr/12 cm of wound. Most preferably the dose of morphine is about 4 mg/4 hr/10 cm of wound.

In accordance with the present invention, the foregoing doses can be readily optimized following the teachings herein based on known pharmacological protocol by those of ordinary skill in the art, with no more than routine optimization. Of course, the preferred lower limit for drug delivery is that necessary to bring about analgesia. The preferred upper limit is that amount which will produce a centrally-mediated effect, i.e., delivery of enough opioid analgesic agent from a peripheral site to produce a centrally-mediated effect, is outside the preferred scope of the invention.

While the foregoing discussion of preferred embodiments specifically mentions morphine, other opioid analgesic agents are envisioned as well. Not all opioid analgesic agents are equianalgesic, i.e., they do not all result in the same degree of analgesia for the same mass of drug. Therefore, when choosing the amount of non-morphine opioid analgesic agent, the amount selected is preferably equianalgesic to the dose of morphine presented above. Equianalgesic doses are well known to those of ordinary skill in the art. In addition, one of ordinary skill in the art would be readily able to determine how to use other opioid analgesics by following the present disclosure. For example, based on the example for morphine given above, one of ordinary skill in the art could, without more than routine experimentation, readily substitute other opioid analgesic agents for morphine. Table 23-6, which appears on page 535 of Chapter 23, of *Goodman and Gilman's Pharmacological Basis of Therapeutics*, Ninth Edition may be used as an aid in determining equianalgesic doses. Notation "c" of the table states:

"Except where noted, dose is the amount that produces approximately the same analgesic effect as 10 mg of morphine administered intramuscularly or subcutaneously."

Thus, the table demonstrates that, applied intramuscularly ("IM" on the Table), 10 mg of morphine provides the same analgesic effect as 130 mg of codeine, 2 mg of butorphanol, or 0.1 mg of fentanyl. In other words, to achieve the same effect, one would use thirteen times (10 mg×13=130 mg) that amount for codeine compared to the amount of morphine required, one fifth of that amount for butorphanol (10 mg×0.2=2 mg), and one one-hundredth (10 mg×0.01=0.1 mg) of that amount for fentanyl. The same types of conversions are appropriately applied in the present invention. Of course, the amount of opioid analgesic agent may be varied or optimized, as necessary. The preferred lower limit for delivery is that amount of opioid analgesic agent needed to produce analgesia. The preferred upper limit is that amount which will produce a centrally-mediated effect, i.e., delivery of enough opioid analgesic agent from a peripheral site to produce a centrally-mediated effect, is outside the preferred scope of the invention.

Preferred embodiments of the present invention comprise surgical structural support elements such as sutures, staples, clips, pins, trocars, chest tubes, foley catheters, and indwelling catheters. Other preferred embodiments envisioned include surgical implants which do not necessarily serve a structurally supportive role, including but not limited to, pills, pellets, rods, wafers, discs, and tablets. The shape of dosage forms of the present invention is not limiting, and is preferably selected considering the needs of the application. For example, a surgical suture may be preferable in those instances in which a deep surgical incision in muscle or fascia has been made, and which needs to be closed with a structural element. Surgical staples or clips may be preferred in a similar situation, the selection preferably depending on the needs and wants of the practitioner. Alternatively, in other preferred embodiments, a shallow wound may require sterile adhesive strips, rather than sutures for closure. In such other preferred embodiments, an implant such as a rod, or several pellets, is preferably placed into the wound prior to closure with the sterile adhesive strips. Again, the choice of shape and embodiment is preferably based on the needs and desires of the practitioner. For example, for those applications in which flexibility is desired, a collection of pellets may be more preferable than a stiff rod. Alternatively, for closure of a surface skin wound in a flexible part of the body, a surgical suture according to the invention may be desirable. The size and shape is not considered limiting, and is preferably selected based on the wants and needs of the practitioner.

Sutures prepared using morphine as the analgesic agent preferably release about 4 mg of morphine per 4 hours per 10 centimeter length of suture. The amount released per length of suture is not crucial, as long as the amount of drug delivered to the wound is within the ranges set forth above. Again, if a different opioid analgesic agent is chosen, the amount used is preferably equianalgesic to that amount of morphine set forth in the ranges described above. However, the dose delivered by the device is preferably less than that necessary to induce systemic analgesia through centrally-located opioid receptors. Obviously, the lower limit is preferably chosen based on that amount necessary to bring about analgesia through peripheral opioid receptors. The amount of drug which is released per length of suture will preferably be varied depending on the preferences of the user or the requirements of the application. For example, for those wounds or incisions in which a great number of "stitches" are needed to close the wound, the amount of opioid analgesic agent released/hr/cm of suture will preferably be less. On the other hand, for those wounds or incisions which require fewer "stitches," a larger amount of opioid analgesic agent will preferably be released from the suture.

Similarly, implants according to the present invention, which include but are not limited to, pills, pellets, rods, discs, etc., are preferably constructed so that an appropriate amount of the device may be placed into the wound to release about 4 mg of morphine/4 hours/10 cm of wound or incision. For example, in one preferred embodiment, two 4-cm rods, which are approximately 0.25 cm in diameter, may be placed into a 10-cm wound, each rod releasing about 2 mg morphine/4 hours. In another preferred embodiment, four 0.5-cm pellets may be spread evenly in a 10-cm wound, each pellet releasing up to approximately 1 mg morphine/4 hours. Alternatively, eight 0.25-cm pellets may be used in a similar manner. The combination of shape and dosage is preferably chosen based on the ability of the combination to deliver the appropriate amount of opioid/hr/cm of wound, the preferred ranges of which are set forth above. Any opioid analgesic agent may be chosen, preferably as long as the dose chosen is equianalgesic to that amount of morphine set forth in the preferred ranges above.

Other preferred embodiments of the present invention include those that are placed on the exterior of the body, but by nature of their placement, allow intimate contact with a source of severe pain. Such preferred embodiments include but are not limited to, bandages, surgical dressings, gauzes, and sterile adhesive strips. Preferred applications of such embodiments include but are not limited to, the treatment of superficial surgical sites, such as that present after the removal of a skin cancer lesion, or a wart. Preferred applications include those in which severe pain is associated with the site of a superficial wound. Other preferred embodiments according to this aspect of the invention include the treatment of burn tissue, which can produce significant pain.

Preferable materials for use in the manufacture of the present invention include both absorbable and nonabsorbable materials. Preferable absorbable materials for use in the present invention include both synthetic and non-synthetic materials. Preferable synthetic absorbable materials include, but are not limited to, polyglycolic acid, copolymers of lactide and glycolide, polydioxanone, polyglactin, poliglecaprone, polyglyconate, and polygluconate. Preferable non-synthetic absorbable materials for use in the present invention include catgut, cargile membrane, fascia lata, collagen, and gelatin. Preferable nonabsorbable materials for use in the present invention include both synthetic and non-synthetic materials. Preferable synthetic nonabsorbable materials for use in the present invention include nylons, rayons, polyolefins, and polyesters. Preferable non-synthetic nonabsorbable materials for use in the present invention include silk, dermal silk, cotton, and linen. The present invention may preferably comprise mixtures of absorbable and nonabsorbable materials, as well as mixtures of synthetic and non-synthetic materials.

The present invention may preferably comprise a polymeric material. In one preferred embodiment, the polymeric material is the sole structural constituent of the invention, such as in polymeric implants, or surgical sutures or staples. In another preferred embodiment, the polymer is an adjunct to the invention, such as in silk sutures which are impregnated with an opioid analgesic agent, and which are coated with a polymer. In such an embodiment, the polymer preferably modifies the release of the opioid from the suture so as to achieve the desired result. In preferred embodiments in which the polymeric material is the sole structural constituent of the invention, the invention is preferably absorbed by the body, as opioid analgesic agent is released over time. In other preferred embodiments, the polymeric material is nonabsorbable and the opioid analgesic agent is released over an extended period of time.

According to the present invention, and in accordance with the desired embodiment, the opioid analgesic agent may be incorporated in any known manner. For example, in a preferred embodiment in which VICRYL (polyglactin) sutures are used, the opioid analgesic agent may be incorporated by dipping the suture in a saturated solution of the opioid, followed by drying. In other preferred embodiments in which other materials are used, the suture material may also be dipped into a saturated solution of the opioid analgesic agent. Alternatively, in other preferred embodiments, the opioid analgesic agent is mixed into a solution of the polymer prior to extruding and spinning into sutures, or prior to casting into implants. The choice for incorporation of the opioid is preferably based on the desires and needs of the user.

In other preferred embodiments, the opioid analgesic agent may be incorporated into a device which becomes a permanent part of a body. For example, the opioid analgesic agent may be incorporated into a cement for use in securing broken bones. In this case, the opioid analgesic agent could be introduced at a site of severe pain, a broken bone, and released over a period of time. Even when the supply of opioid analgesic agent is depleted, the bone cement would continue to serve its structural purpose. U.S. Pat. No. 4,373,217, to DRAENERT, discloses implantation formulations, and its entire disclosure is hereby incorporated by reference as though set forth in full herein. In another preferred embodiment, the opioid analgesic agent may be incorporated into a polymeric film which is used to coat a pin, which is used to secure a broken bone. Again, the opioid would be released over time as the polymeric film dissolved, leaving the pin to hold the bone in place. A similar polymeric film containing an opioid analgesic agent could also be applied to a structural plate for implantation into a body.

Figure 1:
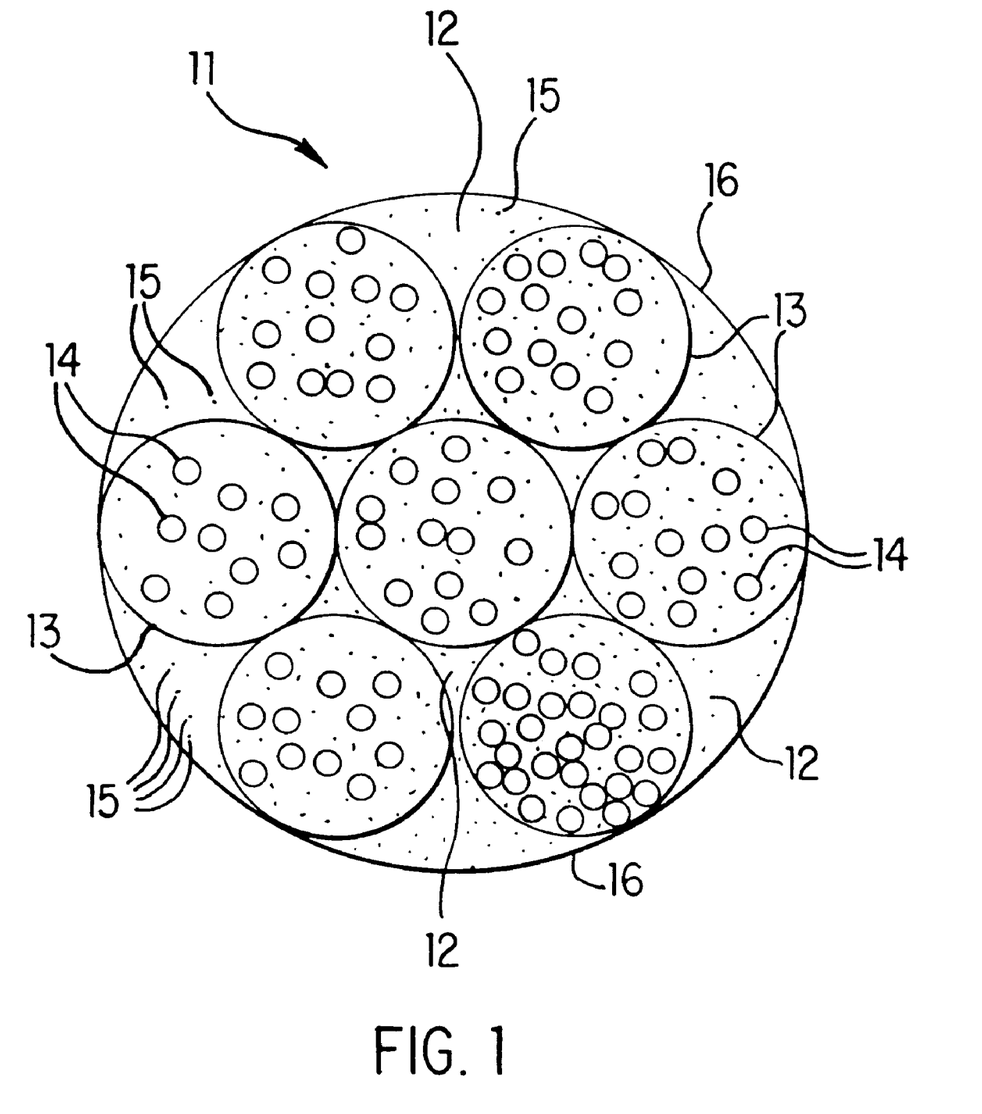
FIG. 1 is a schematic cross-sectional view of an opioid impregnated suture in accordance with one embodiment of the invention, in the form of a multiple strand braided suture.

Referring now to the preferred embodiment of FIG. 1, there is shown a schematic cross-sectional view of a multiple strand braided suture, generally referred to as 11. The interstices 12 between strands 13 and between individual filaments 14 within strands 13 contain analgesic agent 15 (shown as dots in the drawing) which is distributed substantially throughout the suture 11. The analgesic-impregnated suture 11 is preferably optionally surface coated with a polymer and the polymeric coat 16 is continuous and uniform covering over the suture without any substantial penetration into the suture 11. When the suture 11 is used to close a layer of a wound, the analgesic agent is released from the suture into the surrounding tissue over an extended period of time, producing topical analgesia.

Figure 2:
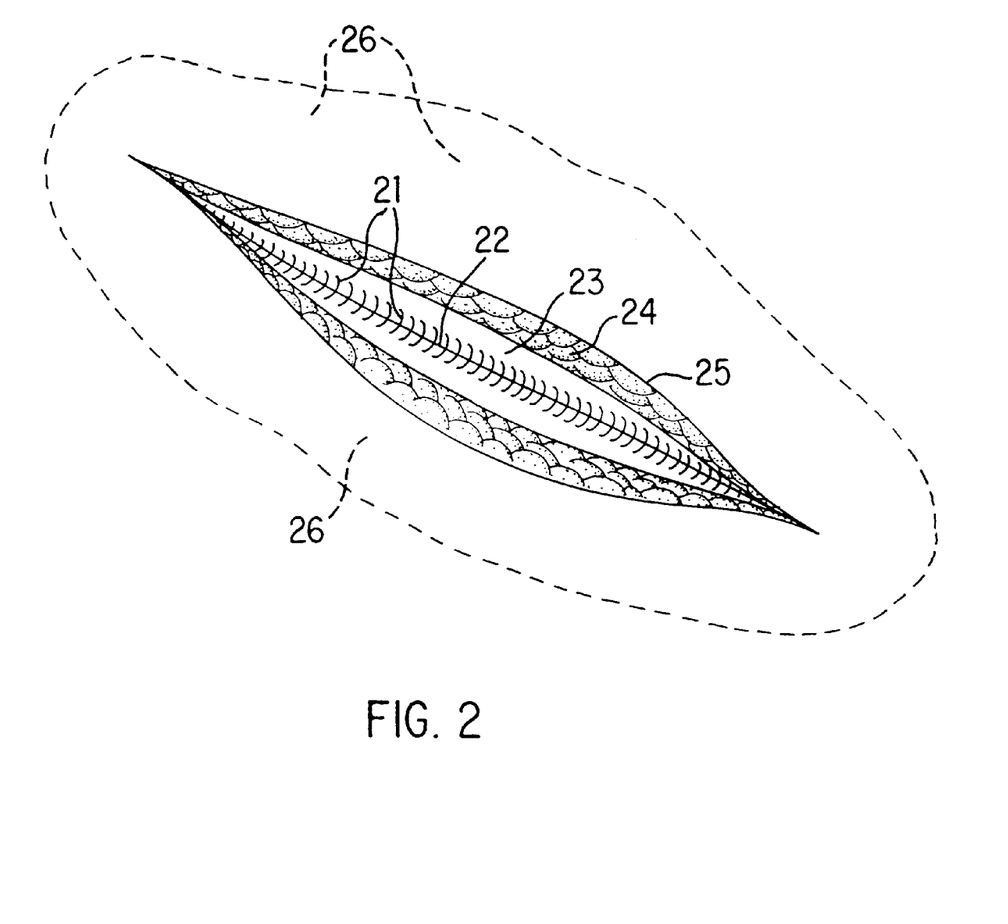
FIG. 2 is a schematic representation of a wound in which an opioid-impregnated suture in accordance with the invention is used to close the wound.

In the preferred embodiment shown in FIG. 2, there is presented one system for treating surgical postoperative pain according to a preferred method of the present invention. In this preferred embodiment, an opioid-impregnated suture 21 is used to close an incision, or wound 22. Inflammation 26 (marked generally by the dotted line) of the area in and surrounding such a wound is a natural part of the healing process. The tissue in the area of the wound includes muscle or fascia 23, fatty tissue 24, and skin 25. FIG. 2 shows a preferable embodiment in which a suture 21 may be used to close the incision in the muscle or connective tissue 23. The incision in the skin 25 may also be closed with a suture similar to the suture 21, or may be closed with an external dressing such as sterile adhesive strips. The suture 21 acts to release the analgesic agent in the immediate vicinity of the inflamed area 26 in continuous manner over a sustained period of time. The amount of the analgesic agent distributed to the area of surgery can be very small (much less than that required for a centrally-mediated effect), but a relatively high concentration of the analgesic agent can develop around the surgical site (in the inflamed area) using only a small-capacity reservoir of the agent. The small amount of analgesic agent required under these conditions, typically a few milligrams, greatly reduces the effect of the analgesic agent at the distal sites within the body (e.g., the brain), practically eliminating the potential for systemic side effects which include nausea, vomiting, cessation of breathing, and even death. By establishing only a local concentration of analgesic agent sufficient to stop the pain at the surgery site, healing can progress much faster. By this procedure, the analgesic agent delivery device containing a few milligrams of morphine, or any other opioid agent, is capable of rendering effects greater than would be expected from the same drugs delivered at much higher doses by other routes of administration (e.g., intravenously or intramuscularly). This results in an unexpectedly high degree of effectiveness for the comparatively small amount of drug utilized.

Figure 3:
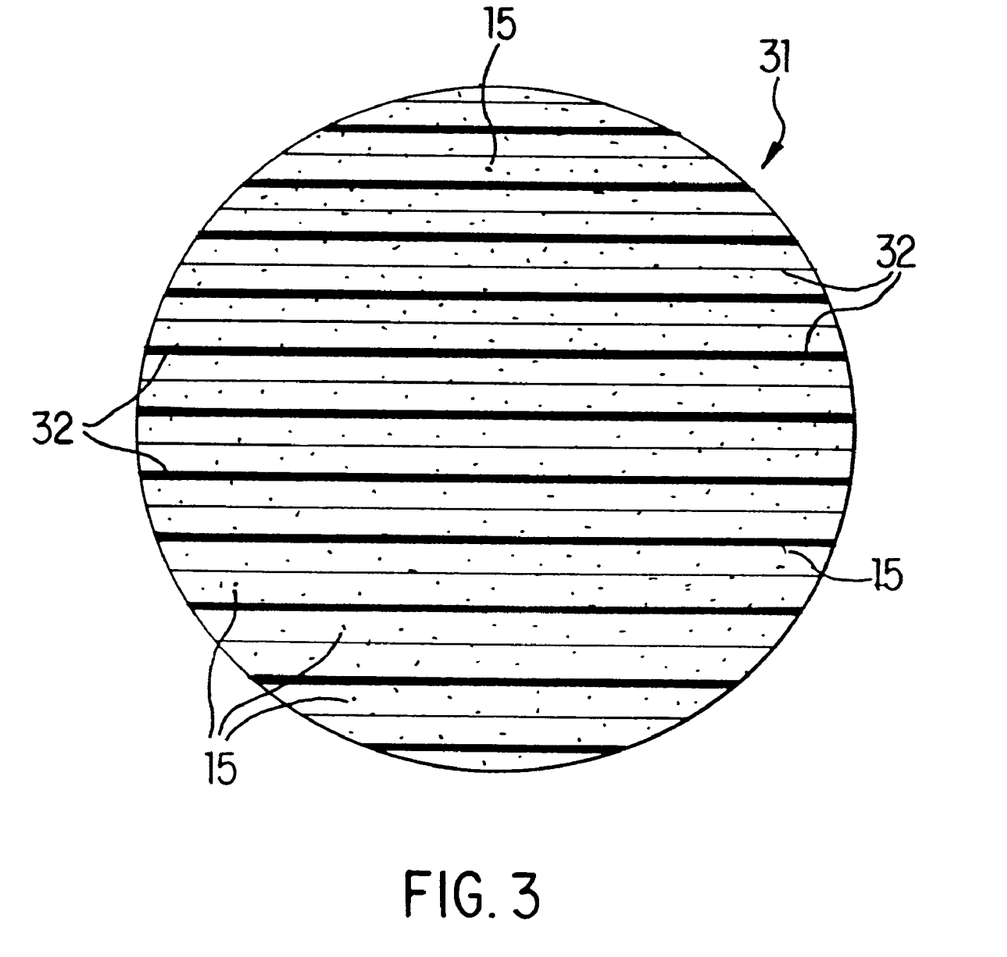
FIG. 3 is a schematic cross-sectional view of a pellet according to the present invention comprising a polymeric matrix impregnated with analgesic agent.

Referring to the preferred embodiment of FIG. 3, there is shown a pellet 31 for opioid analgesic agent 15 according to one embodiment of the invention that includes a matrix 32 of biocompatible, semipermeable polymeric material.

The polymeric material is preferably water soluble. By proper selection of the polymeric material and analgesic materials, the analgesic material will diffuse out of the matrix at a controlled rate over a selected period of time. A wide variety of non-synthetic and synthetic materials such as collagen, cellulosic polymers, glycolic acid polymers, methacrylate polymers, ethylene vinyl acetate polymers, ethylene vinyl alcohol copolymers, polycaptrolactam, polyurethane and polyacetate, and the like, may comprise the polymeric substance for the local delivery device. The device may comprise absorbable or nonabsorbable materials and synthetic or non-synthetic materials, or any combination thereof.

Sutures manufactured from biocompatible polymers according to the present invention may be produced in any manner which is known in the art, including extrusion and spinning.

In preferred embodiments, the polymeric materials may be fabricated into a variety of shapes including slabs, strips, films, ribbons, fibers, pills, pellets, tablets, and rods, and may have various consistencies and physical characteristics including solids, gels, plastics, elastics, micromeshes, and spongy forms, all capable of being introduced into the wound.

Figure 4:
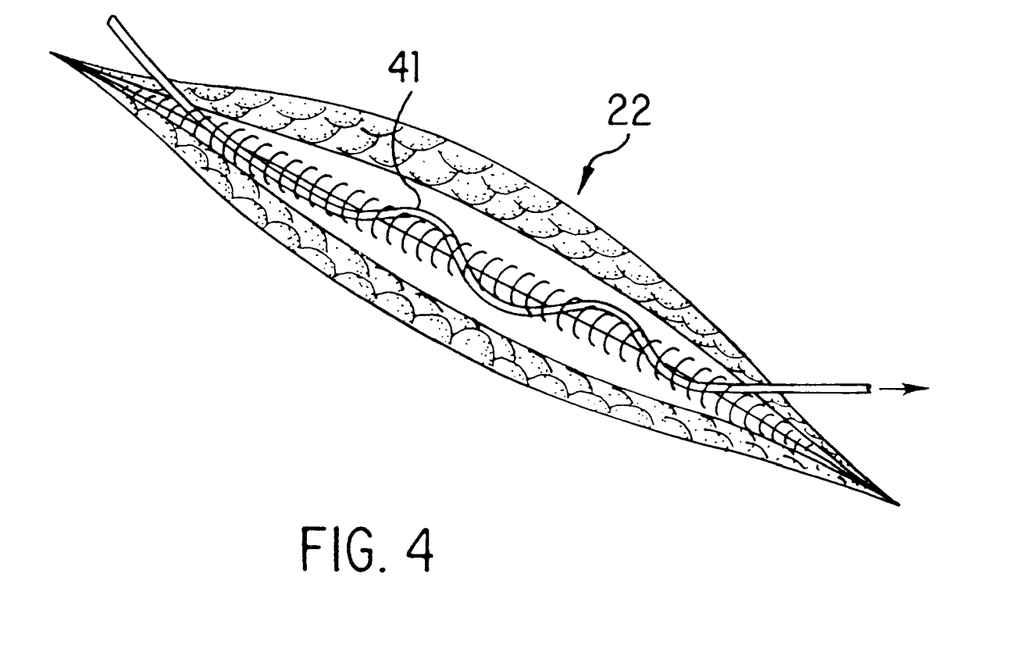
FIG. 4 is a schematic representation of a wound in which a strand of a polymeric matrix impregnated with an analgesic agent in accordance with the invention is placed within the wound.

In the preferred embodiment of FIG. 4, the fiber 41 may be sufficiently formable and flexible to conform to the site to be treated, and this characteristic, in turn, favors the use of soft polymers. Such fiber 41 may be placed alone in the wound 22. The skin incision of the wound may then be closed over the top of the device using any known manner of closing skin wounds, including sutures or staples, or an external closure device such as an adhesive strip.

Figure 5:
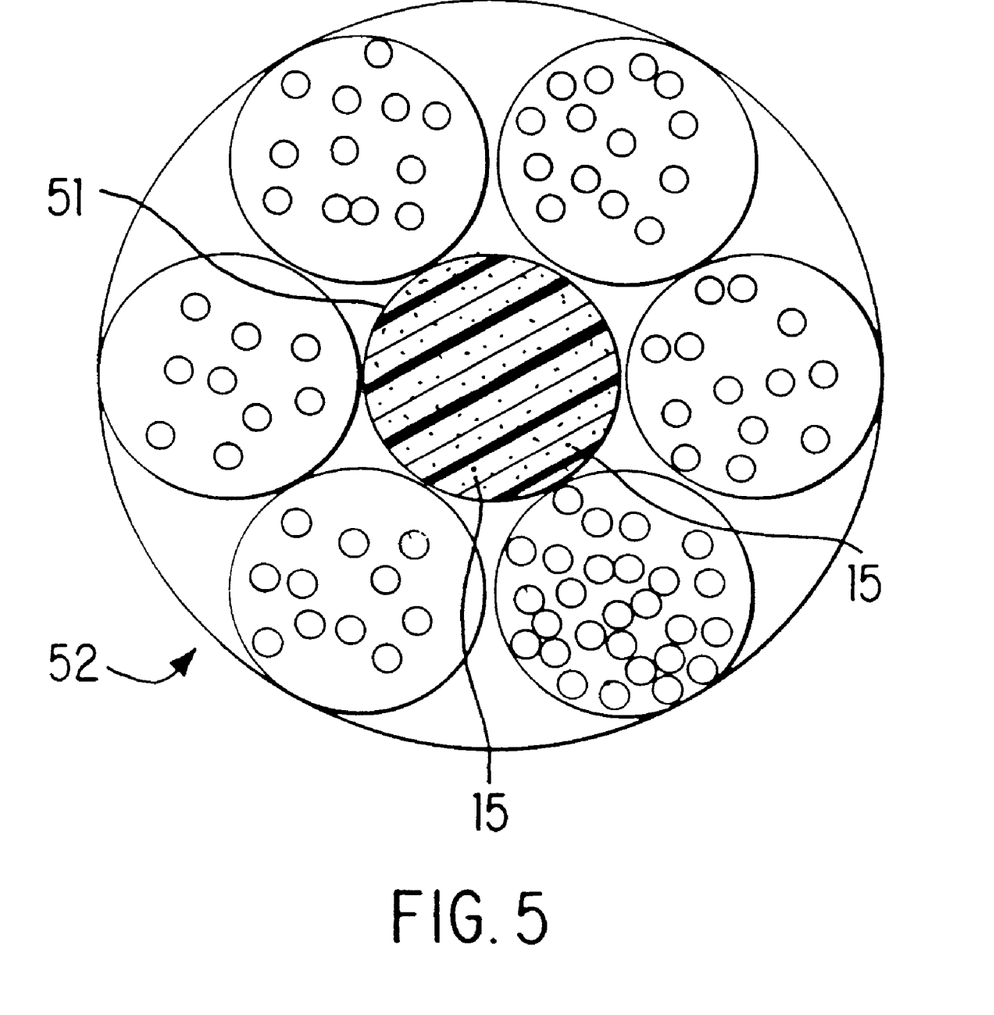
FIG. 5 is a cross-sectional view a polymeric matrix impregnated with analgesic according to the present invention which is integrated in a multiple strand braided suture.

In another preferred embodiment, the polymeric matrix is formed into a strand and is braided into multiple strand suture. FIG. 5 is a diagrammatic cross-sectional representation a strand of polymer 51 which contains the opioid analgesic agent 15 and which is braided into a suture 52.

Figure 6:
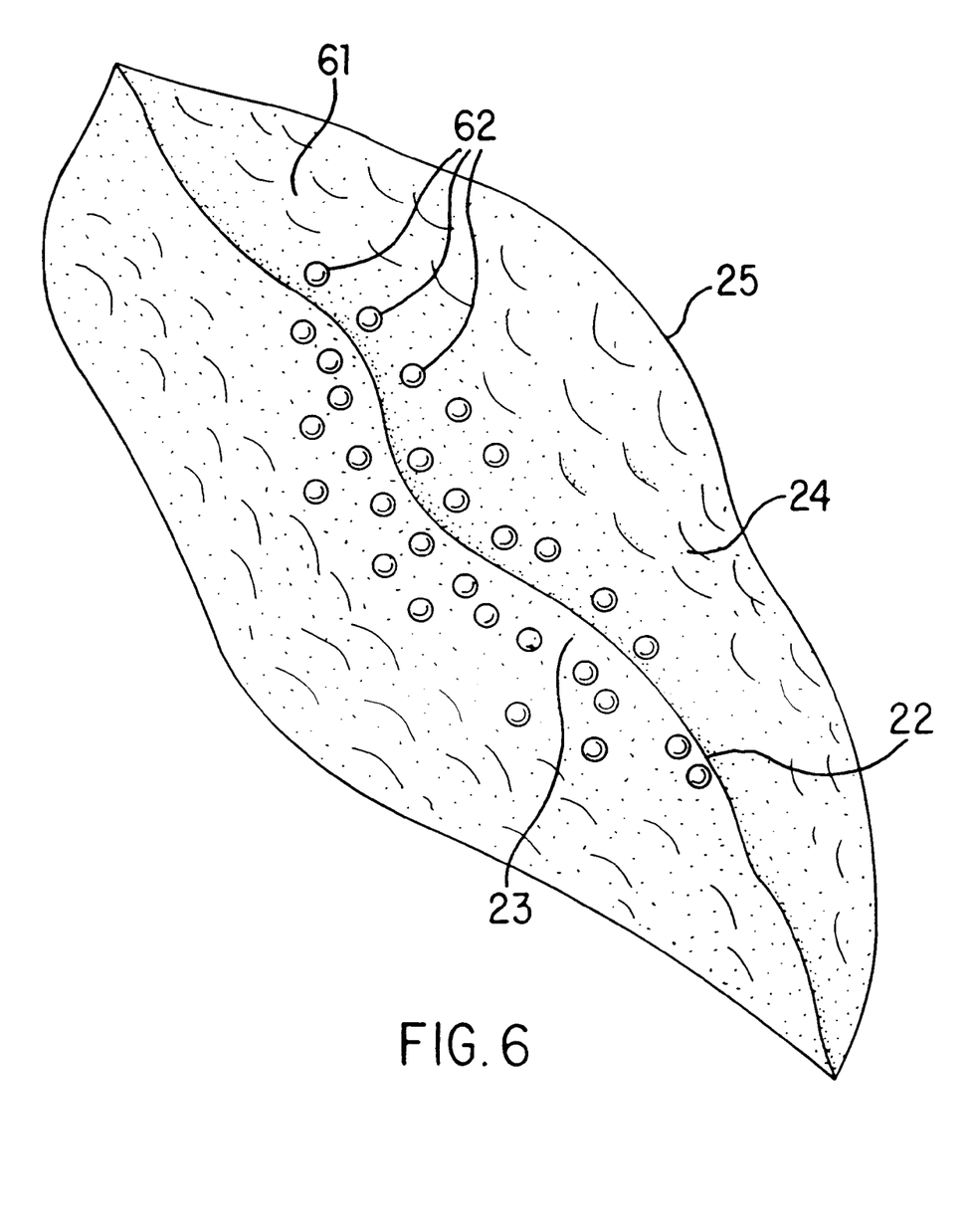
FIG. 6 is a schematic representation of a wound in which pellets of a polymeric matrix impregnated with an analgesic in accordance with the invention are placed within the wound.

FIG. 6 shows another embodiment in which the device is placed directly into the wound 61. In this preferred embodiment, pellets 62 are sprinkled directly into the wound 61 prior to closure of the skin layer 25. The pellets 62 provide for the release of the opioid analgesic over an extended period of time. The tissue in the area of the wound includes muscle or fascia 23, fatty tissue 24, and skin 25, as well as the incision, 22.

In addition to morphine as an analgesic agent for use in the present invention, a wide variety of other opioid analgesic agents (agonist and mixed agonist-antagonist) may be used by delivery in this manner. Examples of suitable analgesics may be found in Chapter 23, "Opioid Analgesics and Antagonists," of *Goodman and Gilman's The Pharmacological Basis of Therapeutics*, Ninth Edition, pages 521–554, the entirety of which is hereby incorporated by reference as though set forth in full herein.

In addition to the fiber described above, the delivery system could be integrated with the sutures used during surgery. Sutures can be either (a) monofilaments (e.g., nylon) and so the suture would be coated with the opioids which would be continuously released over time, or (b) multifilament or braided (e.g., silk, VICRYL, etc.).

The multifilament sutures may comprise multiple strands or fibers which may be twisted, cabled, or braided to form the suture, and the analgesic agent can be disposed in and about the interstices between strands and between the multiple filaments so that such space contains the analgesic agent distributed substantially uniformly throughout the length of the suture thus formed. The impregnated suture may be surface-coated for example, with polymeric material, to form a substantially continuous and uniform covering over the suture. Since the analgesic agent is not required to interact with the suture material as a condition of use, a wide variety of suture compositions may be used. The analgesic agent may comprise anionic, cationic, or nonionic compounds, and may be selected for use with solvents such as water, or alcohol, when necessary or desirable to achieve the desired impregnation of the sutures. In addition, since compositions of analgesic agents and solvents are not required to react with the suture material for effective delivery according to the present invention, a wide variety of compositions of analgesic compounds and solvents are possible, limited by mutual incompatibility of solvents, fiber materials, and analgesic agents.

The analgesic agent may be applied to the delivery device by impregnating or coating the device with a dilute solution of an analgesic agent in a suitable solvent, and thereafter drying the device to remove the solvent and leave a residue of the analgesic agent distributed substantially throughout the polymeric matrix structure of the device. The analgesic agent within the device may comprise up to 50% of the weight of the dried device. The amount of opioid analgesic agent is preferably balanced against the structural needs. Alternatively, the device may be impregnated with the analgesic agent by any known manner including but not limited to, dipping, spraying, stroking, rolling, etc. The impregnated device may be dried. The drying temperature and times are selected to avoid degradation of the polymeric material or the analgesic agent. In a preferred embodiment, a suture strand is passed in a continuous process through an impregnating bath of analgesic agent such as morphine sulfate in alcohol, followed by drying in warm air. The suture thus formed may be used in conventional manner to penetrate adjacent tissue and traverse and close a surgical wound while continuously delivering low-level concentrations of the analgesic agent in and about the surgical site over an extended period of time.

In another embodiment, surgical staples used to close the skin, or laparoscopy trocars which are in close contact with wounds during surgery, may be coated with an analgesic agent in a manner substantially as described above in order to effectively deliver analgesic directly to the surgical or other wound.

Any of the delivery systems set forth herein preferably deliver doses which are set forth above in the preferred dosage ranges. If a different opioid analgesic drug is chosen, the dose delivered should be equianalgesic those doses of morphine set forth above in the preferred dosage ranges. Of course, higher doses may be used. However, the dose delivered by the invention is preferably less than that necessary to induce systemic analgesia through centrally-located opioid receptors.

The foregoing specific embodiments are illustrative of applications in which the analgesic delivery devices of the invention can be employed. Those of ordinary skill in the art will readily understand that other applications are suitable for the analgesic delivery devices of the invention as well.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever.

The entire disclosures of all patents and publications, cited above and below, are hereby incorporated by reference as though set forth in full herein.

Preparation of Single Polyglycolic Acid Strand

Sutures of the present invention can be prepared by following the procedure for the preparation of strands of polyglycolic acid as set forth in expired U.S. Pat. No. 3,991,766, to SCHMITT et al. The following description of the process for producing glycolic acid strands is taken therefrom.

To 100 parts of recrystallized glycolide (melting point approximately 85.0–85.5° C.) is added 0.02 parts of methoxyacetic acid (Aldrich Chemical Company), 0.03 parts phenoldisulfide (Santo-Nox), and 0.03 parts antimony trifluoride. Separate glass tubes are each charged with approximately 20 grams of the mixture, deoxygenated by repeated evacuation and argon purging, then sealed under vacuum and heated to about 185° to 190° C. for about 4.5 hours. Upon cooling, a white opaque polyglycolic acid is produced in a 97.5% yield with a melt viscosity at 245° C. of approximately 5,000 poises. The polymer is reheated and spun into filaments at a temperature of about 230° C. at a speed of about 150 feet per minute. The filaments produced are cooled, then drawn at about 55° C. When drawn to about five times the original length, a preferable filament is produced.

Preparation of a Polyfilamentary Braided Polyglycolic Acid Strand

The polymer prepared as described above is spun into 0.002 inch diameter fibers which are used to form polyfilamentary strands. The fibers are braided into strands which are the size of 00 sutures (about 0.013 inch), and dipped into a saturated aqueous solution of morphine sulfate, or any other appropriate opioid analgesic agent. The strands are vacuum dried at a temperature of approximately 80° C. at less than approximately 1 mm pressure for about one hour, followed by storage in a dry moisture proof container as set forth in U.S. Pat. No. 3,728,839, to GLICK, the entire contents of which is hereby incorporated by reference as though set forth in full herein.

In another preferred embodiment, opioid analgesic is mixed into the reheated polymer, which is prepared as described above, such that the final concentration of morphine sulfate is up to approximately 50% by weight. The polymer/drug mixture is spun into filaments which can be used alone or woven into braided sutures.

The amount of opioid released from the device during use may be varied by the modification of the weight percent of opioid in the device.

Preparation of Surgical Polyglycolic Acid Implants

The opaque polyglycolic acid prepared as above is dissolved in a solvent such as hexafluoroacetone (Aldrich Chemical Company), or hexafluoroisopropanol (Aldrich Chemical Company). An opioid analgesic agent is added to the solution in an amount of up to 50% by weight of the total weight of the polyglycolic acid in the solution. The solution is cast into implants such as pills, pellets, or rods, and vacuum dried, as above. Alternatively, the solution may be cast into the other preferred shapes of surgical staples, clips, hemostats, or intrauterine devices.

The amount of opioid released from the device during use may be varied by the modification of the weight percent of opioid in the device.

Preparation of Polyurethane for Coating Sutures

Coated sutures of the present invention can be prepared by following the procedure for the preparation of a polyurethane coating for sutures as disclosed in expired U.S. Pat. No. 4,024,871, to STEPHENSON. The following description of the process for producing such a polyurethane is taken therefrom.

Polytetramethylene ether glycol (molecular weight approximately 1800) and p,p'-methylenediphenyl diisocyanate (Alpha Research Chemicals and Accessories) are intimately mixed in molar ratio of approximately 1.7:1 (diisocyanate:polyether glycol) and held about 90 to 100 minutes at about 80° C. to about 90° C. to yield an isocyanate-terminated polyether. The isocyanate terminated polyether is cooled and dissolved in N,N-dimethylacetamide (Alpha Research Chemicals and Accessories) to give a mixture containing approximately 45% solids. This mixture is thoroughly agitated for 15 minutes and is conducted to a chamber in which (1) a stoichiometric amount of a mixture consisting of 80 mol % ethylenediamine (Alpha Research Chemicals and Accessories) and 20 mol % 1,3-cyclohexylenediamine in additional dimethylacetamide and (2) approximately 7 mol % diethylamine (Aldrich Chemical Company) (based on total diamines) in dimethylacetamide are added with strong agitation. The mixture is held at a temperature of about 100° C. for about 2 to 3 minutes. The resulting solution of polyurethane contains approximately 36% solids and has a viscosity of about 1800 poises at 40° C. The polymer has an intrinsic viscosity of about 1.15, measured at 25° C. in hexamethylphosphoramide (Aldrich Chemical Company) at a concentration of 0.5 grams per 100 ml of solution. The concentration of the polymer is adjusted to approximately 5% by weight by the addition of N,N-dimethylacetamide, and the resulting solution is used to coat the sutures as follows.

Preparation of Polyurethane Coated Sutures

Nylon surgical sutures (ETHILON, Ethicon) are dipped into a saturated aqueous solution of morphine sulfate. The sutures are vacuum dried overnight to remove any traces of solvent. The polyurethane coating is applied to the opioid-impregnated suture from a solution containing from about 2% to about 20% by weight polymer in a suitable solvent such as N,N-dimethylacetamide. Preferably, the polymer is present at about 3% to about 10% by weight. It is preferable to have the maximum concentration of polymer that is consistent with uniform application. The polymer coating is applied by any known method, including dipping, spraying, wiping, roller coating, etc. The sutures are preferably coated with approximately 3% to approximately 20% by weight of polyurethane polymer. Preferably, the percent by weight of polyurethane in the suture is between approximately 5% and approximately 10%.

The amount of opioid released from the device during use may be varied by the modification of the weight percent of opioid in the device. Alternatively, the weight percent of polymer applied to the suture may be varied as well.

The devices prepared according to the aforementioned procedures are preferably be tested for their ability to release the opioid analgesic agent. Testing may be performed by any known method and suitable methods are described in Chapter 711 of *The U.S. Pharmacopeia XX*, pages 959–960, which is hereby incorporated by reference as though set forth in full herein.

Sutures prepared using morphine as the analgesic agent preferably release from approximately 0.1 mg to approximately 10 mg of morphine per 4 hours per 10 centimeter length of suture. The amount released per length of device is not crucial, preferably, as long as the dose of drug delivered to the wound is in the range of doses set forth in the preferred ranges above. Again, if a different opioid analgesic agent is chosen, the amount used is preferably equianalgesic to those doses set forth in the preferred ranges above. The dose delivered by the invention is preferably less than that necessary to induce systemic analgesia through centrally-located opioid receptors. The amount of drug which is released per length of suture will preferably be varied depending on the preferences of the user or the requirements of the application. For example, for those wounds or incisions in which a great number of "stitches" are needed to close the wound, the amount of opioid analgesic agent released/4 hr/10 cm of suture will likely be less. On the other hand, for those wounds or incisions which require fewer "stitches," a larger amount of opioid analgesic agent will likely need to be released from the suture.

Similarly, implants according to the present invention, which include but are not limited to, pills, pellets, rods, discs, etc., are preferably constructed so that an appropriate amount of the device may be placed into the wound to release about 4 mg of morphine/4 hours/10 cm of wound or incision. For example, in one preferred embodiment, two 4-cm rods, which are approximately 0.25 cm in diameter, may be placed into a 10-cm wound, each rod releasing about 2 mg morphine/4 hours. In another preferred embodiment, four 0.5-cm pellets may be spread evenly in a 10-cm wound, each pellet releasing up to approximately 1 mg morphine/4 hours. Alternatively, eight 0.25-cm pellets may be used in a similar manner. The combination of shape and dosage is chosen based on the ability of the combination to deliver a dose of opioid as set forth in the preferred ranges above. Other opioid analgesic agents may be chosen as well, as long as the dose chosen is equianalgesic to those doses set forth in the preferred ranges above. The amount of opioid analgesic delivered may be higher, with the proviso that the amount delivered is preferably insufficient to produce systemic effects.

What is claimed is:

1. A method of inducing analgesia, comprising delivering, for a period of time which is at least about 1 day, via a surgical suture, a therapeutically-effective amount of an opioid analgesic agent to peripheral opioid receptors, which amount is ineffective for the production of centrally-mediated analgesia.

2. The method of claim 1, wherein said suture comprises a polymeric material.

3. The method of claim 1, wherein said suture comprises an absorbable material.

4. The method of claim 3, wherein said absorbable material comprises a synthetic material.

5. The method of claim 4, wherein said synthetic material is selected from the group consisting of cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof.

6. The method of claim 3, wherein said absorbable material comprises a non-synthetic material.

7. The method of claim 6, wherein said non-synthetic material is selected from the group consisting of catgut, cargile membrane, fascia lata, gelatin, collagen, and combinations thereof.

8. The method of claim 1, wherein said suture comprises a nonabsorbable material.

9. The method of claim 8, wherein said nonabsorbable material comprises a synthetic material.

10. The method of claim 9, wherein said synthetic material is selected from the group consisting of nylons, rayons, polyesters, polyolefins, and combinations thereof.

11. The method of claim 8, wherein said nonabsorbable material comprises a non-synthetic material.

12. The method of claim 11, wherein said non-synthetic material is selected from the group consisting of silk, dermal silk, cotton, linen, and combinations thereof.

13. A method of inducing analgesia, comprising delivering, for a period of time which is at least about 1 day, via an at least partially subdermal drug delivery device, a therapeutically-effective amount of an opioid analgesic agent to peripheral opioid receptors, which amount is ineffective for the production of centrally-mediated analgesia, wherein said device comprises staples or clips.

14. A method of inducing analgesia, comprising delivering, for a period of time which is at least about 1 day, via an at least partially subdermal drug delivery device, a therapeutically-effective amount of an opioid analgesic agent to peripheral opioid receptors, which amount is ineffective for the production of centrally-mediated analgesia, wherein said device is selected from the group consisting of trocars, catheters, and tubes.

15. A drug delivery device for subdermal administration comprising an opioid agonist selected from the group consisting of morphine, depomorphine, heroin, oxymorphone, levorphanol, methadone, meperidine, fentanyl, sufentanil, alfentanil, codeine, hydrocodone, drocode, oxycodone, and mixtures thereof, and a polymeric material, which device releases said opioid analgesic for a period of time which is at least about 1 day, and wherein a unit dosage of the device does not contain enough opioid analgesic agent to produce centrally-mediated analgesia.

16. A drug delivery device for subdermal administration comprising an opioid analgesic and a polymeric material, which device releases said opioid analgesic for a period of time which is at least about 1 day, wherein a unit dosage of the device does not contain enough opioid analgesic agent to produce centrally-mediated analgesia, and wherein said opioid analgesic comprises a partial opioid agonist.

17. The device of claim 16, wherein said partial opioid agonist comprises ethylketocyclazocine.

18. A drug delivery device for subdermal administration comprising an opioid analgesic and a polymeric material, which device releases said opioid analgesic for a period of time which is at least about 1 day, wherein a unit dosage of the device does not contain enough opioid analgesic agent to produce centrally-mediated analgesia, and wherein said opioid analgesic comprises a mixed opioid agonist/antagonist.

19. The device of claim 18, wherein said mixed opioid agonist/antagonist is selected from the group consisting of cyclazocine, nalbuphine, buprenorphine, meptazinol, butorphanol, pentazocine, dezocine, and mixtures thereof.

20. A drug delivery device for subdermal administration comprising an opioid analgesic and a polymeric material, which device releases said opioid analgesic for a period of time which is at least about 1 day, wherein a unit dosage of the device does not contain enough opioid analgesic agent to produce centrally-mediated analgesia, and wherein said polymeric material comprises an absorbable material.

21. The device of claim 20, wherein said absorbable material comprises a synthetic material.

22. The device of claim 21, wherein said synthetic material is selected from the group consisting of polyglycolic acid, copolymers of lactide and glycolide, polydioxanone, polyglactin, poliglecaprone, polyglyconate, polygluconate, and combinations thereof.

23. The device of claim 20, wherein said absorbable material comprises a non-synthetic material.

24. The device of claim 23, wherein said non-synthetic material is selected from the group consisting of gelatin, collagen, and combinations thereof.

25. A drug delivery device for subdermal administration comprising an opioid analgesic selected from the group consisting of morphine, depomorphine, heroin, oxymorphone, levorphanol, methadone, meperidine, fentanyl, sufentanil, alfentanil, codeine, hydrocodone, drocode, oxycodone, and mixtures thereof, and a polymeric material, which device releases said opioid analgesic for a period of time which is at least about 1 day, wherein a unit dosage of the device does not contain enough opioid analgesic agent to produce centrally-mediated analgesia, and wherein a unit dosage is eguianalgesic to from about 0.01 mg morphine/4 hr/10 cm wound to about 8 mg morphine/4 hr/10 cm wound.

26. The device of claim 25, wherein a unit dosage is equianalgesic to from about 2 mg morphine/4 hr/10 cm wound to about 6 mg morphine/4 hr/10 cm wound.

27. The device of claim 26, wherein a unit dosage is equianalgesic to about 4 mg morphine/4 hr/10 cm wound.

28. The device of claim 20, wherein the opioid analgesic agent comprises up to 90% by weight of the device.

29. The device of claim 28, wherein the opioid analgesic agent comprises up to 70% by weight of the device.

30. The device of claim 29, wherein the opioid analgesic agent comprises up to 30% by weight of the device.

* * * * *